United States Patent [19]

Moore

[11] 4,354,837
[45] Oct. 19, 1982

[54] DENTAL APPLIANCE FOR USE IN COMBINATION WITH A SALIVA EJECTOR

[76] Inventor: Charles E. Moore, 365 N. Church St., Tupelo, Miss. 38801

[21] Appl. No.: 325,010

[22] Filed: Nov. 25, 1981

[51] Int. Cl.³ .............................................. A61C 17/04
[52] U.S. Cl. ..................................................... 433/91
[58] Field of Search ........................... 128/276; 433/91

[56] References Cited

U.S. PATENT DOCUMENTS 2,603,870 7/1952 Nordin ................................... 433/94
3,777,756 12/1977 Lohr ...................................... 433/91

Primary Examiner—Robert Peshock

[57] ABSTRACT

The dental appliance of the present invention is to be used in combination with a saliva ejector having a flexible hollow suction tube and a terminal cap secured to one end of the suction tube for forming a saliva tip. The terminal cap includes a plurality of slotted grooves laterally spaced apart in substantial parallel alignment about the periphery of the cap. The dental appliance comprises a collar having a blade-like protrusion and a locking finger including means for engaging any preselected one of said slotted grooves.

5 Claims, 6 Drawing Figures

DENTAL APPLIANCE FOR USE IN COMBINATION WITH A SALIVA EJECTOR

This invention relates to a dental appliance for use in combination with a saliva ejector of the type to be placed in the mouth of a dental patient for drawing saliva.

The basic dental saliva ejector includes a vacuum suction tube composed of flexible plastic with one end adapted to be connected to a source of vacuum and with the opposite end containing an apertured tip adapted for placement in the patient's mouth. Upon the application of vacuum liquid is drawn into the saliva ejector through the apertured tip. Various saliva ejector devices have been developed which are multifunctional serving in addition to the function of drawing saliva to provide various additional functions including support, retraction of the lip, tongue and/or cheek. Such devices are bulky, expensive and, in general, impractical to use. Other dental appliances have been developed as accessory equipment for conventional saliva ejectors. To date these implements have met with limited commercial success due to their inability to reliably prevent the soft tissue in the mouth from blocking the ejector tip or to protect the tongue against abrasion from a rotary dental implement.

The dental appliance of the present invention is adapted to be mounted on a saliva ejector tip for retracting the tongue or cheek from the mandible so as to maintain a clear channel for fluid flow to the ejector tip without interference by the soft tissue in the mouth. The dental appliance of the present invention is inexpensive, disposable and readily adjustable into various fixed positions for assuring positive retraction of the tongue during any dental operatory procedure on a mandibular incisor. The appliance is adjustably attachable to the tip of a saliva ejector over a multiple number of selectively varied positions into which the appliance automatically locks. With the dental appliance locked into any preselected fixed position positive retraction of the tongue or cheek is assured during all dental procedures.

It is, accordingly, an object of the present invention to provide a dental appliance for use in combination with a saliva ejector which guards, protects and assures positive retraction of the tongue or cheek during dental procedures.

It is a further object of the present invention to provide a dental appliance for use in combination with a saliva ejector which will maintain a clear channel for fluid flow to the saliva ejector.

It is an even further object of the present invention to provide a dental appliance for use in combination with a saliva ejector which will increase the visibility of the dentist for performing surgical and/or tooth preparation procedures.

It is another object of the present invention to provide a dental appliance for use in combination with a saliva ejector which is readily mounted to the saliva ejector and locked into selectively adjustable positions.

It is yet another object of the present invention to provide a dental appliance for use in combination with a saliva ejector which is inexpensive and readily expendable for disposable use at the option of the dentist.

Other objects and advantages of the present invention will become apparent from the following detailed description of the invention when read in conjunction with the accompanying drawings of which:

Figure 1:
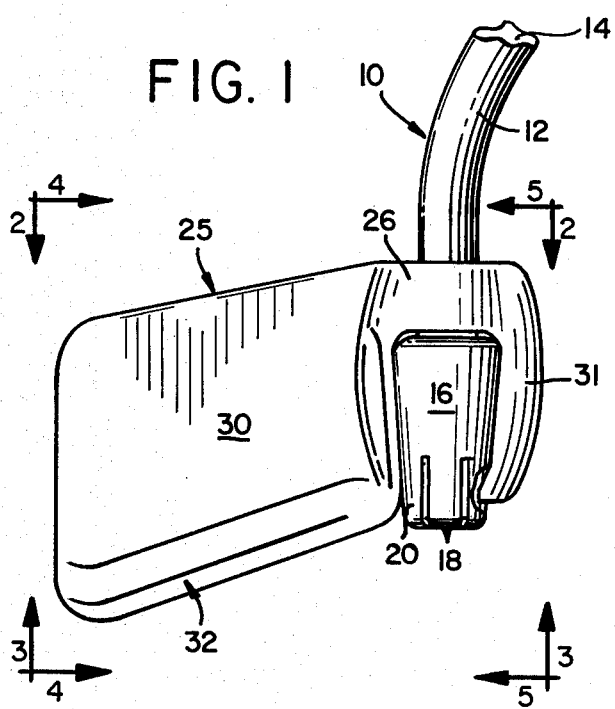
FIG. 1 is a side elevation of the dental appliance and saliva ejector combination of the present invention.
Figure 6:
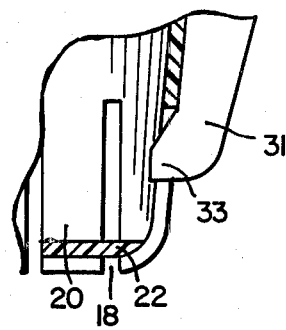
FIG. 6 is an enlarged fragmentary cross-sectional view of the anti-rotational locking arrangement between the dental appliance and saliva ejector of FIG. 1.
Figure 4:
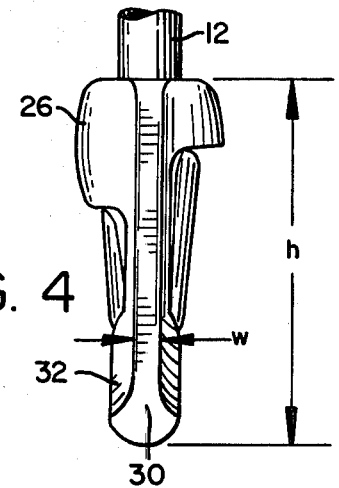
FIG. 4 is a front view of the dental appliance and saliva ejector of the present invention taken along the lines 4—4 of FIG. 1.
Figure 3:
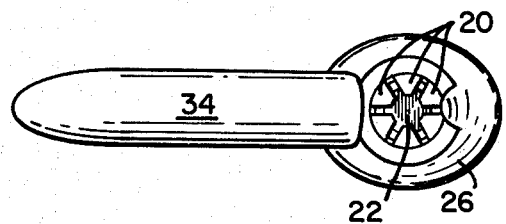
FIG. 3 is a bottom view of the dental appliance and saliva ejector combination of the present invention taken along the lines 3—3 of FIG. 1.
Figure 2:
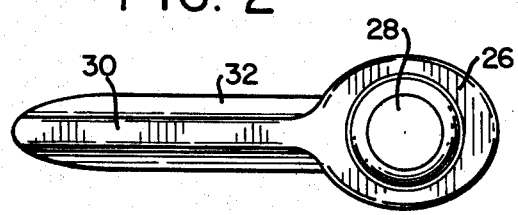
FIG. 2 is a plan view of the dental appliance with the saliva ejector removed taken along the lines 2—2 of FIG. 1.
Figure 5:
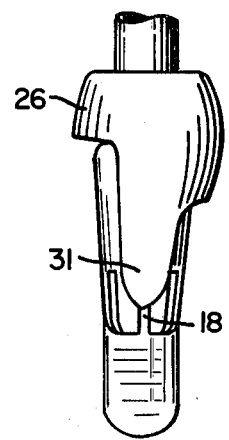
FIG. 5 is a rear view of the dental appliance and saliva ejector of the present invention taken along the lines 5—5 of FIG. 1.

Referring now to FIGS. 1-6 inclusive wherein the numberal 10 designates the saliva ejector including a flexible hollow suction tube 12 of any conventional plastic composition preferably of a polypropylene homopolymer having an open end 14 which leads directly or through a coupling to a source of vacuum (not shown). A terminal cap 16 is secured over the other end of the suction tube 12 for forming a conventional saliva tip upon placement into the mouth of the dental patient. The terminal cap 16 has a multiple number of elongated longitudinally extending slotted grooves 18 which are laterally spaced apart in substantial parallel alignment about the periphery of the cap 16. The spacing between the slotted grooves 18 is not material to the present invention. The slotted grooves 18 form fingers 20 with their ends curled over and secured to a flat plate 22 for forming a relatively blunt tip open only through the slotted grooves 18. Saliva is passed through the openings formed by the slotted grooves 18 into the suction tube 12 from whence the saliva is drawn by the vacuum system.

A dental appliance 25 is coupled to the terminal cap 16 of the saliva ejector 10. The dental appliance 25 has a collar 26 with a bore 28 adapted to slidably fit over the tube 12. The diameter of the bore 28 must necessarily be larger than the diameter of the tube 12 but should, preferably, not be larger than the circumference of the terminal cap 16.

The collar 26 has a relatively flat blade-like protrusion 30 extending from one side thereof and a depending locking finger 31 extending from another side thereof. The blade-like protrusion 30 is of a substantial dimension in height "h" relative to its thickness or width "w". The long height dimension of the protrusion 30 is oriented in a substantially vertical disposition to fit between the lateral border of the tongue and the mandibular arch. The blade-like protrusion 30 widens out at the bottom end thereof adjacent the blunt end of the cap 16 to form a pedestal 32 with a relatively horizontal base 34 adapted to fit under the lateral border of the tongue and mandible so as to resist any tendency in the dental appliance 25 to shift position. The base 34 also provides a foot rest for the tongue which improves the comfort of the patient.

The locking finger 31 has a fin-like projection 33 adapted to enter and engage any of the slotted grooves 18 upon being positioned thereover.

In operation the suction tube 12 is supplied to the dentist as a straight member. The dentist bends the tube 12 into any desired shape prior to use. The collar 26 of the dental appliance 25 is preferably slipped over the suction tube 12 before it is bent with the wide base 34 of the blade 30 facing down. The collar 26 is then pressed down to force the locking finger 31 to slide over the terminal cap 16. The collar 26 may be rotated about the terminal cap 16 until the fin-like projection 33 is aligned with any desired one of the slotted grooves 18 as selected by the dentist. The fin-like projection 33 is then snap locked into the selected groove 18. The suction tube 12 may then be bent into a desired configuration generally in the form of a question mark with the curved region hung on the patient's jaw to support the saliva ejector 10.

What is claimed is:

1. A dental appliance for use in combination with a saliva ejector having a flexible hollow suction tube and a terminal cap secured to one end of the suction tube and including a plurality of slotted grooves laterally spaced apart in substantial parallel alignment about the periphery of the cap, said appliance comprising a collar having a bore adapted to fit over said suction tube, a relatively flat blade-like protrusion extending from one side of said collar, a depending locking finger extending from another side of said collar including means for engaging any preselected one of said slotted grooves upon depressing said collar.

2. A dental appliance for use in combination with a saliva ejector as defined in claim 1 wherein said blade-like protrusion has a height substantially longer in dimension than its width, with the height dimension oriented in a relatively vertical disposition to fit between the lateral border of the tongue and the mandibular arch.

3. A dental appliance for use in combination with a saliva ejector as defined in claim 2 wherein said locking finger means comprises a fin projecting from said finger and adapted to be manually snapped into any selected one of said slotted grooves for locking the appliance into the saliva ejector.

4. A dental appliance for use in combination with a saliva ejector as defined in claim 3 wherein said blade-like protrusion has an end adjacent the terminal cap forming a pedestal with a relatively horizontal base adapted to fit under the lateral border of the tongue and mandible.

5. A dental appliance for use in combination with a saliva ejector as defined in claim 4 wherein said appliance is composed of a polypropylene composition.

* * * * *